(12) United States Patent
Taulu et al.

(10) Patent No.: US 6,876,196 B1
(45) Date of Patent: Apr. 5, 2005

(54) DETERMINING A POSITION OF OBJECTS IN A PREDETERMINED COORDINATE SYSTEM

(75) Inventors: Samu Taulu, Helsinki (FI); Lauri Parkkonen, Helsinki (FI); Matti Kajola, Helsinki (FI)

(73) Assignee: Elekta Neuromag Oy, Helsinki (FI)

( * ) Notice: Subject to any disclaimer, the term of this patent is extended or adjusted under 35 U.S.C. 154(b) by 0 days.

(21) Appl. No.: 10/665,543

(22) Filed: Sep. 22, 2003

Related U.S. Application Data

(63) Continuation of application No. PCT/FI02/00225, filed on Mar. 19, 2002.

(30) Foreign Application Priority Data

Mar. 19, 2001 (FI) .............................................. 20010558

(51) Int. Cl.⁷ .............................. G01B 7/14; G01S 5/04; A61B 5/05
(52) U.S. Cl. ............. 324/247; 324/207.23; 324/207.17; 700/153; 600/409; 600/424
(58) Field of Search ................................. 702/150–153; 324/207.12, 207.17, 207.22, 207.23, 232, 247, 207.26; 600/424, 409, 407, 595

(56) References Cited

U.S. PATENT DOCUMENTS

| | | | |
|---|---|---|---|
| 5,729,129 A | 3/1998 | Acker | 324/207.12 |
| 5,747,996 A | 5/1998 | Fuchs | 324/207.17 |
| 6,188,355 B1 | 2/2001 | Gilboa | 324/207.17 |

Primary Examiner—Jay Patidar
(74) Attorney, Agent, or Firm—Squire, Sanders & Dempsey L.L.P.

(57) ABSTRACT

The invention relates to a method and device by means of which the location and position of an object may be determined in relation to another object by electromagnetic signals. In the arrangement in accordance with the invention there are two objects to the one of which there are attached signal sources, i.e. transmitters that generate electromagnetic signals, and the other object contains one or more receivers for measuring the transmitter signals. Usually the object containing transmitters is the one whose location or position is of interest and which is the object of the measurement. For example, in MEG measurements the object associated with the transmitters is the head of a human being on whose surface the transmitters are placed. By means of the arrangement in accordance with the invention is possible to find out the location and position of the head, in which case the location of the signals generated by the brain may be found out and utilized when examining the brain activity. The transmitters are also used to measure the signals emanating from the brain.

15 Claims, 1 Drawing Sheet

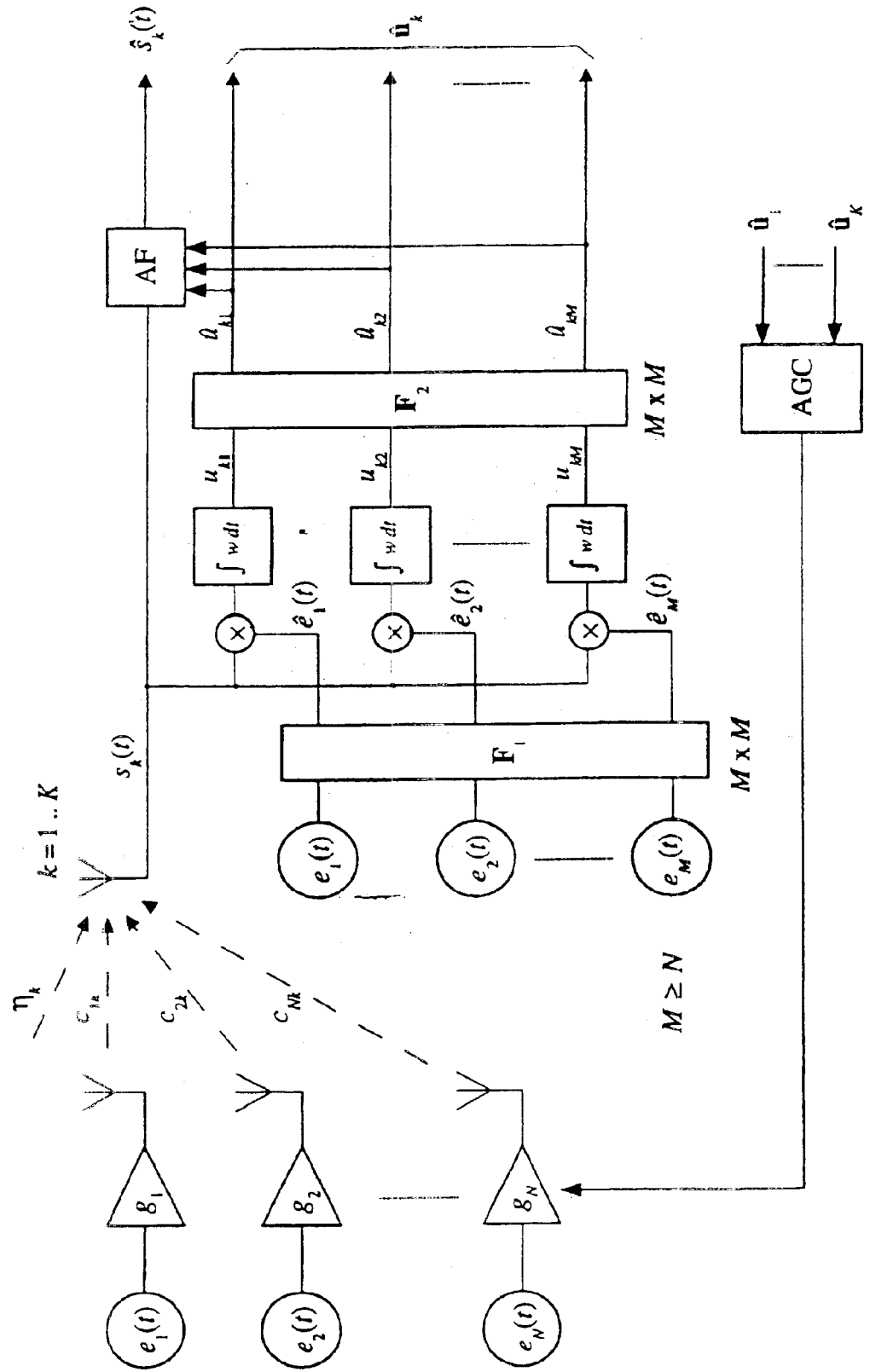

DETERMINING A POSITION OF OBJECTS IN A PREDETERMINED COORDINATE SYSTEM

This is a Continuation of International Application No. PCT/FI02/00225 filed Mar. 19, 2002, which designated the U.S. and was published under PCT Article 21(2) in English.

FIELD OF THE INVENTION

The present invention relates to the determining of the position of objects. In particular, the present invention relates to a new and improved method of determining the location and position of objects in relation to each other by means of electromagnetic signals.

BACKGROUND OF THE INVENTION

The location method based on electromagnetic signals has been described, in a very general way independent of the subject of application, e.g. in patent publications U.S. Pat. Nos. 5,747,996, 4,346,384 and DE3326476. In one embodiment, the device comprises a set of signal sources, a set of receivers and one or more signal generators which are used to generate a set of transmitter signals known as concerns their tense to be transmitted by signal sources. In addition, the aforementioned patent publications disclose an analysis method for processing the output signals of the receivers and for using them in calculating the position of an object in relation to another object. Common to the devices described in the publications is that the signal transmitters have been attached to the object in a manner geometrically rather restricted.

In addition, in publications U.S. Pat. Nos. 5,747,996 and 4,346,384 one requires that the signal sources are orthogonal between themselves. Thanks to the orthogonality, there is no correlation between the signals transmitted by the signal sources, i.e. the signals do not have an effect on each other that would disturb the determining of location. In addition, in publication U.S. Pat. No. 5,747,996 one requires that the receivers are coils placed on the same level. The geometric requirements are used to facilitate and speed up the signal analysis and to eliminate the possible sources of error having effect on the positioning result.

In the co-ordinate system of an object, the location method based on known signal sources is used e.g. in magnetoencephalography (MEG), in which one measures the weak magnetic fields generated by the neural activity of a human being or other organism that are dependant on time and place. Based on the measured magnetic field values, one tries to locate the source areas that generated the observed field. In magnetoencephalography, the head of a testee is as close as possible to the set of detectors i.e. receivers consisting of extremely sensitive supraconducting detectors, the geometry of which is known. The position of the head in relation to the measuring device is determined using, as known signal sources, coils attached to the surface of the head the magnetic field generated by whom may be approximated by the field of a magnetic dipole.

As receivers, the measuring detectors of the measuring device are used that are also used for the receiving and measuring of the actual brain signals to be measured. The basic principles of the method have been described e.g. in publications *SQUID' 85*: Super-conducting Quantum Interference Devices and their Applications, 1985, pages 939–944 and *Proceedings of the 7th International Conference on Biomagnetism*, 1989, pages 693–696.

The actual MEG measurements are usually implemented as repetition measurements, in which a response generated by the brain, followed e.g. after a certain stimulus is measured several times successively, and a mean value of the measurement results time-locked in relation to the stimulus is calculated. When using the mean value of the measurement results the effect of noise may be attenuated by a factor which is vice versa proportional to the square root of the number of repetitions. One problem with the repetition measurements is their long duration, because of which the head of a testee may move during the measurement. From this automatically follows that the position of the source of the response generated by the brain changes in relation to the measuring device in the middle of measurement, thereby causing errors to the final analysis.

Traditionally, the position of the head has been determined solely in the beginning of the measurement so that each head positioning coil has been activated and the magnetic field generated has been measured one by one, in which case the location method has been rather slow. After the location, the testee has been asked not to move his head until the end of the repetition measurement.

The errors resulting from the movement of head during the measurement may be avoided by a continuous measurement of position. In that case, one has to be able to use the measuring device simultaneously also for the measuring of other transmitter signals than the one to be generated in the positioning. One way to eliminate the effect of the transmitter signals on the useful signal to be measured, i.e. on the response signal generated by the brain is to set the frequencies of the transmitter signals far away from the frequency band to be examined and to filter measurement data appropriately in the frequency plane. This kind of solution is presented in publication *Biomag*2000, 12*th International Conference on Biomagnetism, Book of Abstracts*, p. 188, Peters, H. et al. Another solution is the filtering of the transmitter signals from the output signals of the receivers by subtracting the shares corresponding to the transmitter signals from the measured signals, in which case one has to known the strengths and wave shapes of the transmitter signals to be measured.

When trying to determine the position of an object constantly or repeatedly at short intervals the signal transmitters have to be activated simultaneously and one has to be able to tell the difference between the simultaneous components generated by different transmitters and the measurement signals. The method should distinguish the frequency components as efficiently and accurately as possible using a data collection time as short as possible. In a generally used distinction method the frequencies and the data collection time are adjusted so that the signal components are orthogonal between themselves at the time interval being examined. If the phase of the transmitter signal is known, then the amplitude of each signal component is achieved directly by calculating the projection of the signal vector consisting of the measurement results for the basis vector corresponding to the signal component being examined that consists of the computational values of the basis function known as concerns its frequency. Applications based on the orthogonality of the basis vectors have been described e.g. in publications "The use of an MEG device as a 3D digitizer and a motion correction system", de Munck et al *Proceedings of the* 12*th International Conference on Biomagnetism*, Helsinki, Finland. In this description, the effect of the non-orthogonality has been taken into account on a principal level. In the positioning method described, the orthogonalisation of the transmitter signals, however, substantially reduces the amount of computation associated with the positioning, so in an implementation in practice, the transmitter signals are orthogonalised.

The requirement of orthogonality sets requirements to the frequencies to be used as well as to the data collection time, and in addition, the supposition of orthogonality for non-orthogonal signals causes great errors in the computed amplitude coefficients and thereby also in the positioning. In the signal analysis described above one tries to use signals collected from a time interval as short as possible in order that the positioning would be as real-time as possible and the movement of the objects would be as slight as possible during the data collection of the positioning measurement. Dependable positioning measurements have been made in magnetoencephalography using a data collection time of solely 100 ms.

Even at a time interval like this objects may move, which makes the positioning result worse. Due to the possibly large movement of the objects, the strengths of the signals measured by the receivers may vary from the lowest limit of a signal to being observed rapidly up to the upper limit of the dynamic area of the receivers. The variation may be significant especially in small distances, since the strength of a measured signal is vice versa proportional to the third power of the distance of objects. In addition to this, the same transmitters may be used in different measurements for objects for very different sizes and located in different distances in relation to the transmitters. The repeated succeeding of the measurements to be made in different situations requires that the strengths of the transmitter signals measured by the receivers constantly remain within certain limits. The problem has been solved by using an adjustment algorithm which controls the power of the transmitters in such a way that the amplitudes of the signals measured by all the receivers remain above a certain lowest limit and below a certain upper limit. The return switching, or feedback, of the transmitter signals has been described e.g. in patent publication U.S. Pat. No. 5,747,996.

OBJECTIVE OF THE INVENTION

The objective of the present invention is to eliminate the drawbacks referred to above or at least significantly to alleviate them. One specific objective of the invention is to disclose a new type of method for implementing the positioning measurement as quickly and accurately as possible. One further objective of the present invention is to disclose a measuring method which is numerically simple and efficient and in which the non-orthogonality of the signal sources does not do any harm to the accuracy of the final result. Yet another objective of the present invention is to disclose a computation method which enables one to calculate the position of an object almost in-real time and thus eliminate the errors caused by the movement of the object in the actual measurement, e.g. in magnetoencephalography. It is still another objective of the present invention to a disclose a new kind of correction method of computation by which the measured distributions of amplitudes may be corrected in order to remove the errors resulting from the non-orthogonality and possible other disturbances from the amplitude or distribution of amplitudes determined to the signal, depending on the number of receivers.

DESCRIPTION OF THE INVENTION

The invention relates to a method which enables one to determine the position and location of an object in relation to another object by means of electromagnetic signals. In the arrangement in accordance with the invention there are two objects, of which to the one there are attached signal sources, i.e. transmitters which generate electromagnetic signals, and the other object contains one or more transmitters for measuring the transmitter signals. Usually the object containing transmitters is the one whose location or position is of interest and which is the object of the measurement. For example, in biomagnetic measurements the object associated with the transmitters is the head of a human being or another restricted part of the body on whose surface the transmitters are placed. By means of the arrangement in accordance with the invention it is possible to find out the location and position of the head, in which case the source areas of the signals generated by the brain may be shown in the co-ordinates of the head. The same receivers are used to measure the signals generated both by the brain and the transmitters.

The signal transmitters located in known locations in the co-ordinate system of the transmitter object, may be activated so as to generate signals of different frequencies either simultaneously or by turns so that the frequencies and wave shapes are optional. Due to this, the arrangements associated with the transmitters, e.g. as regards the geometry and the signals used, become considerably more simple than before. The amplitudes of the signals generated by different transmitters are measured using the receivers of another device the mutual geometry of which is either known beforehand, or is determined during the positioning. As concerns the actual measurements, it is sufficient that one is able to find out the mutual geometry of the transmitters and receivers, since the placement of the transmitter in the object is usually known. Thus, when the geometry of the receivers and transmitters as well as the amplitude distribution of the signals sent from the transmitters is known, the actual object signals measured from the object by receivers and their original location may be determined in relation to the transmitters and thus in relation to the object.

The invention is based on the use of signals generated by electromagnetic or acoustic transmitters attached to an object and measured by receivers of another object in an analysis as a result of which the relative location or position of the objects or both can be calculated. The positioning may be constant using a rapid computation method of amplitudes, and in successive measurements, vectors possibly partly temporally overlapping and generated by the measured signal values.

In the location method of the invention one allows the non-orthogonal basis vectors of the transmitter signals, in which case the frequencies, wave shape and data collection time of the signals to be transmitted may be selected quite freely. The non-orthogonal projection method to be used in the calculation and accentuated by basis vector inputs is numerically a very fast and accurate operation compared to the other signal analysis methods used. Unlike in the article of de Munck referred to above, in this invention the amount of the additional computation caused by the non-orthogonality of the transmitter signals is in practice negligible. In the method it is possible to use transmitter signals the phases of which are unknown. In that case, the phases may be solved by calculating the amplitudes for appropriately selected basis vectors which can have a difference in phase in relation to the actual basis vectors of the transmitter.

By means of the method of the invention it is possible to further estimate, in addition to the transmitter signals, the amplitudes of known sources of interference, in which case their interfering effect may be removed. Interferences of this kind include specially the basic frequency of the network frequency and its harmonious components.

In order that the matching of the measured and computed amplitudes would be as precise as possible one needs information on the interference and noise appearing on the channels. Since these may vary as a function of time, it is advantageous to measure the parameters in question in conjunction with the positioning measurement. This may be implemented by subtracting the estimated signals from the measured signals and by using the power of the remaining signal in some frequency band.

According to one embodiment of the invention it is possible to estimate signal components that differ from the actual signal shapes to be estimated that are generated by transmitters or known sources of interference.

The receivers may also be used during the positioning measurement to measure also other signal sources than the transmitter signals. This is implemented by subtracting the share of the computed transmitter signal amplitudes from the output signal of each receiver at each moment of time. Thanks to the invention, the subtraction succeeds better than before because the estimation of the amplitudes and phase of signals is more precise than in the previously known devices. The filtering enables a continuous positioning when measuring also other signals than transmitter signals.

The strengths of the transmitter signal amplitudes to be observed in the receivers may be adjusted by return switching, or feedback, in which one takes into account the signals measured by the whole set of receivers. In this way, a sufficient signal noise ration is ensured in every measurement situation.

The accuracy of the positioning of the invention may be improved by measuring the interference level of the signal by subtracting from the measured signals the signals determined by means of known basis signal forms. The differential signal thus remaining tells about the fact of how dependable each estimate is, and this information may be used for making the matching more precise by taking into account the noise level. The noise level may also be measured by estimating the signal or signals that differ from the shapes of the transmitter signals and from those of the interferences known by us, e.g. a network frequency interference. By estimating an amplitude for this kind of signal by the method of the invention, information is gained on the fact of how much the presumed model of the signal space differs from reality.

The advantage of the present invention over prior art is that by means of the arrangement of the invention, the clarifying of the amplitude distributions of signals sent by a certain set of transmitters and received by a certain set of receivers, with one or more receivers, becomes more precise and effective than before. Likewise, thanks to the invention, the choosing of the signals to be transmitted becomes considerably more free than before, specially in terms of frequency and phase. Thanks to the invention, the signals do not have to be orthogonal with each other.

Further, thanks to the invention it is possible to take into account, e.g. in the MEG measurements, the possible movements of the head during the measurement of the actual useful signal. In addition, the invention allows the elimination of external sources of error in order to improve the accuracy of the measurement results.

Further, the method and device of the invention can be easily modified, and the correction calculation to be implemented in the invention may be implemented at a measuring and calculation step each time most suitable.

BRIEF DESCRIPTION OF THE DRAWING

FIG. 1 illustrates a measuring device arrangement in accordance with the present invention.

DETAILED DESCRIPTION OF THE INVENTION

In the following section, the invention will be described by the aid of a detailed example of its embodiment with reference to the accompanying drawing which schematically represents one measuring device arrangement in accordance with the invention.

In the following section, one mode of implementation of the invention will be described. The drawing illustrates, on a principal level, the measurement arrangement of the invention that comprises a transmitter part $g_1, \ldots, g_n$ and receiver structure which comprises a set of receivers $1, \ldots, K$. The drawing shows only one receiver antenna, but it is obvious to a person skilled in the art how an arrangement of several antennas is implemented in accordance with the drawing. The receiver is used to measure the amplitudes of the transmitter signals $c_{1k}, c_{2k}, \ldots, c_{Nk}$ and of the possible interference $\eta_k$. In the symbols of the signals, parameter k refers to the measurement result to be obtained k from one sent signal due to the fact that each signal is received, seen from the starting point, with k receiver.

In addition in the drawing there is shown the return switching, or feedback, AGC controlling the transmitters as an input to which there are the final measured signal amplitudes $\hat{u}_k$. Based on the obtained amplitudes, the return switching, or feedback, controls the transmission power of the transmitters so that the signal-noise ratio constantly remains on the desired level in order to achieve the best possible measurement result. Further, in the drawing there is shown a filter AF, which is arranged in between the receivers $1, \ldots, k$ and the output of the measuring device in order to filter the singals transmitted by the transmitters from the actual useful signal $s_k(t)$.

In the measuring arrangement there is, according to the above-mentioned, a measuring device consisting of K receivers that is simultaneously stimulated by a signal source g attached to the object to be positioned by N. The receiver k is used to collect signal over the time interval T, and over the signal components $e_1(t), \ldots, e_M(t)$ (M>N associated with different transmitters g when wishing to estimate from the transmitter signals also other than their basic components $1, \ldots, N$). For measuring the amplitudes, a signal vector consisting of signal values collected from different moments of time is first projected for basis vectors corresponding to different frequencies as well as for basis vectors being at the same frequency with these that have a difference in phase of about 90 degrees in relation to the previous basis vectors.

In the drawing, the calculation of the projections has been described by means of certain integrals of the products of the signals measured in the manner of continuous functions and of those of the basis vectors over the time T. It must be noted that in a digital implementation, instead of the integrating, summing is used as a numerical integrating that is in fact an estimate of a constant integrating. The digital implementation is, however, in no way restricted from the application possibilities of the present invention.

If desired, the integrand may be accentuated by some window function w. The M dimensional projection vector u obtained after the projection is corrected by matrix $F_2$, which is an (M×M) dimensional matrix depending on the basis vectors so that $\hat{u}=F_2*u$, in which case $\hat{u}$ is a vector containing the amplitude coefficients of the transmitter signals and those of the identical signals being 90 degrees in a different phase with these as well as those of other wave shapes to be estimated.

The formal mathematical grounds of the correction are as follows. The signal vector consisting of the signal values measured at different moments of time is marked by s:, and the matrix containing the basis vectors as horizontal vectors is marked by E, in which case the measured signal is of the form $s=E^{t*}\hat{u}$, from which a pseudo inverse solution $\hat{u}=\text{inv}(E*E^T)*E*s=\text{inv}(E*E^T)*u$ is obtained, in which case T refers to the transpose of the matrix, and inv( ) to the inverse matrix of the matrix. In that case, the matrix $F_1=\text{inv}(E*E^T)$ and $F_1$ is a unit matrix. The correction required by the non-orthogonality may also be done solely to the basis vectors by using matrixes $F_1=\text{inv}(E*E^T)*E$ and $F_2=$ is a unit matrix, or together both to the basis vectors and projection vectors so that $F_1$ and $F_2$ together form the correction operation. Based on the signal amplitudes measured on different channels it is possible to calculate the relative location or position of objects, or both.

The matrixes $F_1$ and $F_2$ are the same to all the K receivers, so only the projection vector u has to be calculated separately for different receivers, and thus the amount of the additional computation resulting from the non-orthogonality of the transmitter signals is very small. Based on the signal amplitudes measured on different channels it is possible to calculate the relative location on position of the objects, or both.

Since it is possible to measure with the device the amplitudes of arbitrary signal components, the signals used in the above-mentioned description and generated by a stationary object may be replaced with a larger set of basis vectors that are able to represent the wave shapes generated by a moving object. The movement may be modelled e.g. by amplitude modulating the original signal by wave shapes differing from standard ones. This makes it possible to determine the location even of a moving object more precisely and thus take into account the change in the signal amplitudes due to the movement of the object.

The filter AF subtracts from the signal measured at each moment of time the amplitudes of the transmitter signals $c_1$, ..., $c_N$ and the ones of the counterparts of these transferred in time, so the location measuring based on the signals of the transmitters does not do any harm to the actual simultaneous measuring.

The return switching, or feedback, AGC is implemented by calculating the RMS values of each measured signal from time interval T over the set of transmitters 1 . . . K and by adjusting based on this the transmission power of individual transmitters so that the maximum of the estimated signal components over the set of receivers remains approximately standard.

The invention is not restricted merely to the examples of its embodiments referred to above, instead many variations are possible within the scope of the inventive idea defined by the claims.

What is claimed is:

1. A method for determining the location and/or orientation of an object in a predetermined coordinate system, in which method in the object there is arranged a set of signal sources in a known manner in relation to the co-ordinate system of the object, the method comprising:

transmitting a predetermined signal from the signal sources, receiving the signal transmitted from the signal sources with a receiver which comprises signal receivers, computing the location and/or orientation of the object based on received amplitudes of the signals, determining the amplitudes of the received signals, said amplitudes being independent of each other, by computationally taking into account the correlation between the transmitted signals, said transmitted signals being transmitted simultaneously and having arbitrary waveforms, determining each signal source separately from the independent amplitudes, and computing the location and/or orientation of the object at the time interval being examined based on the independent amplitude distributions associated with the signal sources by adjusting numerical amplitudes of the signal sources to the received amplitudes measured using the receiver, said adjusting the numerical amplitudes performed by setting the geometrical free parameters of the signal sources and/or of the receiver to values by which the difference between the calculated and measured amplitude distributions is at its smallest.

2. The method according to claim 1, wherein computing the location and/or orientation of the signal sources in the co-ordinate system of both the object and the receiver from values set to free parameters, and computing the location and/or orientation of the object in relation to the receiver by using known locations of the signal sources.

3. The method according to claim 2, wherein in order to determine an individual signal source:

generating the product of a signal to be estimated for each signal specifically and of a signal received by the receiver, integrating the products over a predetermined time T in order to obtain a preliminary result for the measured amplitudes sent by the signal sources, and generating the product of the preliminary result and of the correction coefficient, in which the correction coefficient is a quantity describing the correlation between the signals sent from different signal sources, in order to obtain the amplitude of the received signal for each signal specifically.

4. The method according to claim 3, wherein the products are accentuated by a window function w.

5. The method according to claim 4, wherein using signal forms of known sources of interference as the estimated signal.

6. The method according to claim 2, wherein generating the product of the signal to be estimated, of the correlation efficient and of the received signal, in which the correction coefficient is a quantity describing the correlation between the signals sent from different signal sources, and integrating the products over a predetermined time T in order to obtain a measuring result for the measured amplitudes of the signals sent by the signal sources.

7. The method according to claim 2, wherein generating the signal product of the signal to be estimated and a chosen coefficient, generating the product of the received signal product and of the received signal, generating the products of the obtained signal product and of the received signal, integrating the products over a predetermined time T in order to obtain a preliminary result for the measured amplitudes of the signals sent by the signal sources, and generating the product of the preliminary result and of a correction coefficient, in which the correction coefficient is a quantity describing the correlation between the signals sent from different signal sources and the effect of the chosen coefficient, in order to obtain the amplitude of the received signal for each signal specifically.

8. The method according to claim 1, further comprising sending a signal in a sine form from the signal sources, and using in the computation as the estimated signal a signal of almost the same form as the sent signal.

9. The method according to claim 8, wherein using in the computation a second signal being at the same frequency with the sent signal that has a difference in phase in relation to the estimated signal.

10. The method according to claim 1, further comprising receiving useful signal by means of the receiver, and filtering the sent signals from the useful signal by the signal source.

11. The method according to claim 1, further comprising estimating signals that correspond to the signals of the signal sources attached to a moving object in a predetermined manner for estimating the motion of the object.

12. The method according to claim 1, wherein the determination of the location and/or orientation of the object is repeated in order to determine the relative location of the object by repeating temporally overlapping measuring periods.

13. The method according to claim 1, further comprising generating a feedback from the obtained amplitudes to the signal sources, and controlling the transmission power of the signal sources by means of the feedback.

14. The method according to claim 1, further comprising subtracting the signals computed at the received signals, and specifying a measuring result by means of a remaining signal.

15. The method according to claim 1, further comprising estimating at least one signal that differ from the signals of the signal sources or from those of the known sources of interference, and specifying the location result based on the obtained measuring result.

* * * * *